US00PP11009P

United States Patent [19]

Davino, Jr.

[11] Patent Number: Plant 11,009

[45] Date of Patent: Jul. 20, 1999

[54] CHRYSANTHEMUM PLANT NAMED 'WARM SANDY'

[76] Inventor: Louis Davino, Jr., 160 Disbrow Hill Rd., Hightstown, N.J. 08520

[21] Appl. No.: 09/044,759

[22] Filed: Mar. 20, 1998

[51] Int. Cl.[6] ..... A01H 5/00

[52] U.S. Cl. ..... Plt./296

[58] Field of Search ..... Plt./295, 296, 286

*Primary Examiner*—Howard J. Locker

*Attorney, Agent, or Firm*—C. A. Whealy

[57] ABSTRACT

A distinct variety of Chrysanthemum plant named 'Warm Sandy', characterized by its uniformly mounded plant habit; relatively large daisy-type inflorescences that are about 7 cm in diameter; attractive bronze-colored ray florets; numerous inflorescenes per plant; early flowering; and excellent garden performance.

1 Drawing Sheet

BACKGROUND OF THE INVENTION

The present invention relates to a new and distinct variety of Chrysanthemum plant, botanically known as *Dendranthema grandiflora* and referred to by the variety name 'Warm Sandy'.

The new Chrysanthemum is a naturally-occurring mutation of the *Dendranthema grandiflora* 'Sandy' (disclosed in U.S. Plant Pat. No. 7,531). In September, 1994, the new Chrysanthemum was discovered by the inventor in a controlled environment in Hightstown, N.J., within a population of plants of 'Sandy'. The selection of this plant was based on its significantly darker ray floret color compared to plants of 'Sandy'. Besides ray floret color, there are no other horticultural differences between plants of the new Chrysanthemum and 'Sandy'.

Asexual reproduction of the new Chrysanthemum by terminal cuttings taken in a controlled environment in Alva, Fla., has shown that the unique features of this new Chrysanthemum are stable and reproduced true to type in successive generations.

BRIEF SUMMARY OF THE INVENTION

The new Chrysanthemum has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Warm Sandy'. These characteristics in combination distinguish 'Warm Sandy' as a new and distinct Chrysanthemum:

1. Uniformly mounded plant habit.
2. Relatively large daisy-type inflorescences that are about 7 cm in diameter.
3. Attractive bronze-colored ray florets.
4. Numerous inflorescences per plant.
5. Early flowering.
6. Excellent garden performance.

BRIEF DESCRIPTION OF THE PHOTOGRAPHS

The accompanying photographs illustrate the overall appearance of the new Chrysanthemum.

The photograph at the top of the sheet comprises a side perspective view of a typical flowering plant of 'Warm Sandy'.

The photograph at the bottom of the sheet comprises a close-up view of typical inflorescences of 'Warm Sandy'. These photographs show the colors as true as it is reasonably possible to obtain in colored reproductions of this type. Floret and foliage colors in the photographs may differ from the actual colors due to light reflectance.

DETAILED BOTANICAL DESCRIPTION

In the following description, color references are made to The Royal Horticultural Society Colour Chart except where general terms of ordinary dictionary significance are used. The following observations and measurements describe plants grown in Salinas, Calif., under conditions which approximate those generally used in commercial garden Chrysanthemum production. One unrooted cutting was directly stuck in a 15-cm container and plants were grown in a greenhouse with night interruption lighting for two weeks during late May/early June. At the end of the night interruption lighting period, plants were pinched (terminal apices removed). Three days later, plants were moved into an outdoor production area. Plants flowered about seven weeks later. Measurements and numerical values represent averages for typical flowering containers.

Botanical classification: *Dendranthema grandiflora* 'Warm Sandy'.

Commercial classification: Daisy-type garden chrysanthemum.

Parentage: Naturally-occurring mutation of *Dendranthema grandiflora* 'Sandy'.

Propagation:

*Type*.—Terminal tip cuttings.

*Time to rooting*.—Seven to ten days with soil temperatures of 21° C.

*Rooting habit*.—Fine, fibrous and well-branched.

Plant description:

*Appearance*.—Perennial herbaceous daisy-type garden Chrysanthemum. Inverted triangle. Stems initially upright, then somewhat spreading giving a uniformly mounded appearance to the plant. Freely branching; about eight lateral branches develop after removal of terminal apex (pinching). Numerous secondary lateral branches develop at every node.

*Plant height*.—About 26 cm.

*Foliage description*.—Leaf arrangement: Alternate. Length: About 5.75 cm. Width: About 5 cm. Apex: Mucronate. Base: Attenuate. Margin: Palmately lobed, sinuses parallel. Texture: Upper and lower surfaces slightly pubescent. Veins prominent on lower surface. Petiole length: About 1.4 cm. Color: Young foliage upper surface: 147A. Young foliage lower surface: 147B. Mature foliage upper surface: 147A. Mature foliage lower surface: Darker than 147B. Venation upper surface: 147A/147B. Venation lower surface: 147B.

Inflorescence description:

*Appearance*.—Daisy-type inflorescence form with oblong-shaped ray florets. Inflorescences borne on terminals above foliage, arising from leaf axils. Disk and ray florets arranged acropetally on a capitulum. One inflorescence per terminal with numerous inflorescences per plant.

*Flowering response*.—Under natural conditions, plants flower in the autumn. Plants exposed to 1.5 to 2 weeks of long day/short night conditions after planting followed by short day/long night conditions flower about 48 days later.

*Inflorescence size*.—Diameter: About 7 cm. Depth (height): About 1.1 cm. Diameter of disc: About 1.6 cm.

*Ray florets*.—Shape: Oblong, flat, recurved with subsequent development. Length: About 3.2 cm. Width: About 8 mm. Apex: Rounded to dentate. Margin: Entire. Texture: Smooth, glabrous. Orientation: Slightly upright to horizontal, curved downward with subsequent development. Number of ray florets per inflorescence: About 60. Color: When opening: Upper surface: Background of 15A with reddish overtones of 172A. Lower surface: 13B/13C. Fully opened inflorescence: Upper surface: Background of 15A with reddish overtones of 172A. Lower surface: 13B/13C.

*Disc florets*.—Shape: Enlarged tubular, apex dentate. Length: About 7 mm. Width: Apex: About 2 mm. Base: About 1 mm. Number of disc florets per inflorescence: Numerous. Color: Immature: 154A. Mature: Apex: 17A. Mid-section: Light green. Base: White.

*Peduncle*.—Aspect: Flexible, strong, angled about 50° to the stem. Length: First penducle: About 7 cm. Fourth peduncle: About 9.5 cm. Texture: Pubescent. Color: 143A.

*Reproductive organs*.—Androecium: Present on disc florets only. Anther color: 17A. Pollen: Amount: Moderate. Color: 17A. Gynoecium: Present on both ray and disc florets.

Disease resistance: No known Chrysanthemum diseases observed to date on plants grown under commercial production conditions.

Seed production: Seed production has not been observed.

It is claimed:

1. A new distinct variety of Chrysanthemum plant named 'Warm Sandy', as illustrated and described.

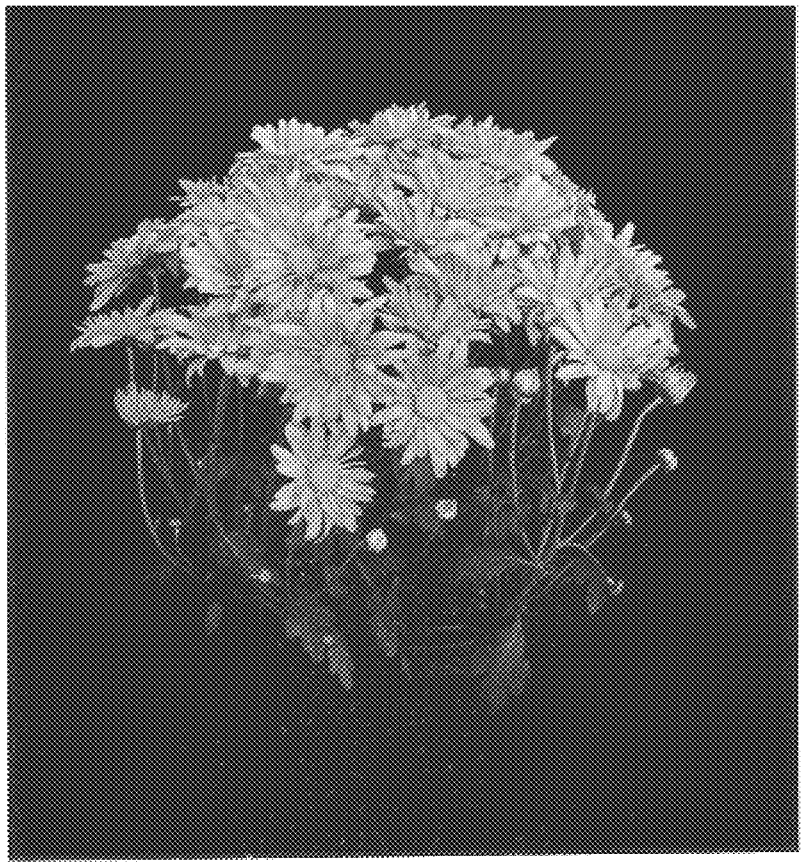
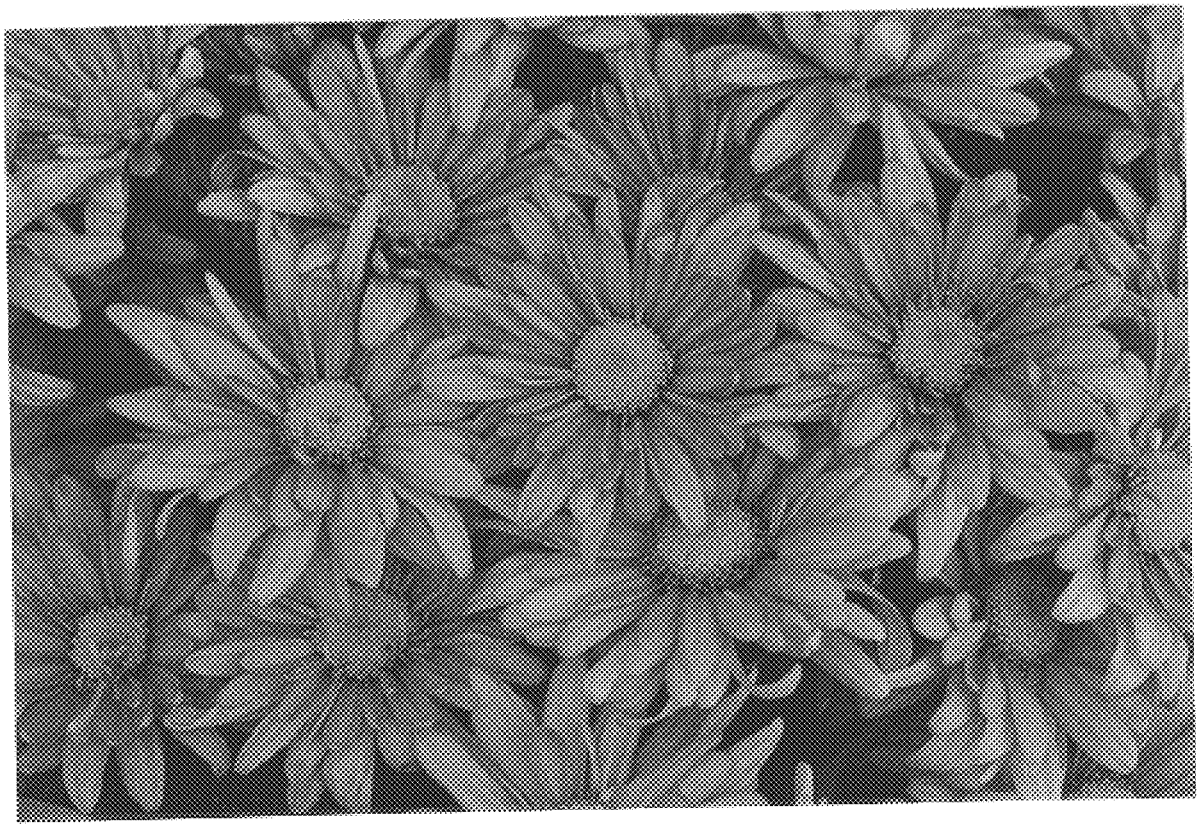

* * * * *